US012699104B2

(12) United States Patent
Minamino et al.

(10) Patent No.: US 12,699,104 B2
(45) Date of Patent: Aug. 4, 2026

(54) HEART FAILURE MARKER

(71) Applicants: NATIONAL UNIVERSITY CORPORATION KAGAWA UNIVERSITY, Kagawa (JP); SHIONOGI & CO., LTD., Osaka (JP)

(72) Inventors: Tetsuo Minamino, Kagawa (JP); Shota Yokoyama, Kagawa (JP); Ryo Kawakami, Kagawa (JP)

(73) Assignees: NATIONAL UNIVERSITY CORPORATION KAGAWA UNIVERSITY, Kagawa (JP); SHIONOGI & CO., LTD., Osaka (JP)

( * ) Notice: Subject to any disclaimer, the term of this patent is extended or adjusted under 35 U.S.C. 154(b) by 935 days.

(21) Appl. No.: 17/774,292

(22) PCT Filed: Nov. 6, 2020

(86) PCT No.: PCT/JP2020/041513
§ 371 (c)(1),
(2) Date: May 4, 2022

(87) PCT Pub. No.: WO2021/090909
PCT Pub. Date: May 14, 2021

(65) Prior Publication Data
US 2022/0390468 A1 Dec. 8, 2022

(30) Foreign Application Priority Data

Nov. 6, 2019 (JP) .................................. 2019-201842

(51) Int. Cl.
*G01N 33/68* (2006.01)
*G01N 33/70* (2006.01)
*G01N 33/74* (2006.01)
(52) U.S. Cl.
CPC ......... *G01N 33/6893* (2013.01); *G01N 33/70* (2013.01); *G01N 33/74* (2013.01); *G01N 2333/575* (2013.01); *G01N 2800/325* (2013.01)
(58) Field of Classification Search
CPC .. G01N 33/493; G01N 33/68; G01N 33/6893; G01N 33/70; G01N 33/74; G01N 2333/575; G01N 2800/325; G01N 2800/50; G01N 2800/52; A61B 5/028; A61B 5/7275; Y10T 436/147777
USPC ......................................... 436/63, 86, 87, 98
See application file for complete search history.

(56) References Cited

U.S. PATENT DOCUMENTS

| | | | | |
|---|---|---|---|---|
| 2010/0159478 A1* | 6/2010 | Brozovich | ......... | G01N 33/6893 435/7.1 |
| 2011/0008805 A1* | 1/2011 | Urdea | .................... | G01N 33/74 435/7.92 |
| 2013/0085079 A1* | 4/2013 | Gill | .................... | G01N 33/6893 506/18 |
| 2014/0038203 A1* | 2/2014 | Arthur | ............... | G01N 33/6893 435/7.1 |
| 2014/0147867 A1* | 5/2014 | Arnold | ............... | G01N 33/6893 435/7.92 |
| 2015/0133326 A1* | 5/2015 | McManus | .......... | G01N 33/6893 435/6.12 |
| 2015/0293124 A1* | 10/2015 | Kas | ........................ | A61P 13/12 514/44 A |
| 2016/0123995 A1* | 5/2016 | Rouet | .................... | G01N 33/74 435/7.92 |
| 2018/0143208 A1* | 5/2018 | Rouet | ................ | G01N 33/6893 |

FOREIGN PATENT DOCUMENTS

| | | |
|---|---|---|
| JP | 2007-327921 | 12/2007 |
| JP | 2016-520843 | 7/2016 |
| JP | 2017-526924 | 9/2017 |
| JP | 2020-051911 | 4/2020 |
| WO | 2014/195456 | 12/2014 |
| WO | 2016/030209 | 3/2016 |

OTHER PUBLICATIONS

Yokoyama et al. Circulation, Abstract 11452, vol. 140, No. Suppl. 1, Nov. 11, 2019.*
Yokoyama et al. Internal Medicine, vol. 59, Nov. 15, 2020, pp. 2839-2847.*
International Search Report issued Jan. 12, 2021 in International (PCT) Application No. PCT/JP2020/041513.
Nishijima et al., "Circadian rhythm of plasma and urinary angiotensinogen in healthy volunteers and in patients with chronic kidney disease", J Renin Angiotensin Aldosterone Syst, 2014, No. 15, vol. 4, pp. 505-508.
Rafiq et al., "Renal Sympathetic Denervation Suppresses de novo Podocyte Injury and Albuminuria in Rats with Aortic Regurgitation", Circulation, 2012, No. 125, vol. 11, pp. 1402-1413.
Katsurada et al., "Novel sandwich ELISA for human angiotensinogen", Am J Physiol Renal Physiol, 2007, No. 293, pp. F956-F960.
Suzaki et al., "Quantification of human angiotensinogen by a novel sandwich ELISA", Peptides, 2006, No. 27, vol. 11, pp. 3000-3002.
Erika E. Nishi et al., "Renal denervation reduces sympathetic overactivation, brain oxidative stress, and renal injury in rats with renovascular hypertension independent of its effects on reducing blood pressure", Hypertension Research, 2018, vol. 42, No. 5, pp. 628-640.
Daniela Patinha et al., "Diabetes-induced increase of renal medullary hydrogen peroxide and urinary angiotensinogen is similar in normotensive and hypertensive rats", Life Sciences, 2014, vol. 108, No. 2, pp. 71-79.

(Continued)

*Primary Examiner* — Maureen Wallenhorst
(74) *Attorney, Agent, or Firm* — Wenderoth, Lind & Ponack, L.L.P.

(57) ABSTRACT

A method for measuring heart failure risk, including:
(A) measuring an angiotensinogen amount value of urine collected from a subject; and
(B) comparing an angiotensinogen amount value of urine previously collected from the subject with the angiotensinogen amount value measured in (A).

9 Claims, 3 Drawing Sheets

(56)                    References Cited

OTHER PUBLICATIONS

Pierre Lantelme et al., "Effects of Dietary Sodium and Genetic Background on Angiotensinogen and Renin in Mouse", Hypertension, 2002, vol. 39, No. 5, pp. 1007-1014.

Maryam Afkarian et al., "Urine matrix metalloproteinase-7 and risk of kidney disease progression and mortality in type 2 diabetes", Journal of Diabetes and Its Complications, 2015, vol. 29, No. 8, pp. 1024-1031.

Supplementary Extended European Search Report issued Feb. 12, 2024 in corresponding European Patent Application No. 20885827. 4.

Joseph L. Alge et al., "Urinary angiotensinogen predicts adverse outcomes among acute kidney injury patients in the intensive care unit", Critical Care, vol. 17, No. 2, pp. 1-9, 2013.

Özcan Örsçelik et al., "Relationship between intrarenal renin-angiotensin activity and re-hospitalization in patients with heart failure with reduced ejection fraction", The Anatolian Journal of Cardiology, vol. 19, pp. 205-212, 2018.

Ha Yeon Kim et al., "Chronic Kidney Disease. Lab Methods, GFR Measurement, Urine Proteomics", Nephrology Dialysis Transplantation, vol. 31, Supplement 1, pp. i163, 2016.

Partial Supplemental European Search Report issued Nov. 14, 2023 in corresponding European Patent Application No. 20885827.4.

* cited by examiner

Urinary AGT(μg/g Cre)

NT-proBNP(pg/ml)

HEART FAILURE MARKER

TECHNICAL FIELD

The present disclosure relates to a heart failure marker, a method for measuring heart failure risk, and the like.

BACKGROUND ART

In our country where the population is aging, a prevalence of heart failure is expected to further rise in the future, and the number of patients with chronic heart failure is expected to increase to 1.3 million in 2035. This is overlapped with a disease state of heart failure in which emergency visit and readmission due to acute exacerbation are repeated, so that an increase in burden on medical system is expected. This state is also called "heart failure pandemic" and is feared. In particular, there are many problems in how a site of primary care physician (local medical care or home medical care) who can be a first receiver of a patient with acute exacerbation should handle.

Since it is said that prognosis of heart failure is additively deteriorated by repetition of acute exacerbation events, the prognosis of heart failure may be improved if appropriate measures can be taken at the time of occurrence of an event at that time. Therefore, it is important to perform acute phase treatment with chronic phase treatment in mind. Prevention of readmission due to heart failure exacerbation together with improvement in mortality rate is one of major targets of treatment of heart failure.

PRIOR ART REFERENCES

Non-Patent Documents

[Non-patent Document 1] Nishijima Y, et al., J Renin Angiotensin Aldosterone Syst 2014, 15:505-508.
[Non-patent Document 2] Rafiq K, et al., Circulation 2012, 125:1402-1413.
[Non-patent Document 3] Katsurada A, et al., Am J Physiol Renal Physiol 2007, 293:F956-960.
[Non-patent Document 4] Suzaki Y, et al., Peptides 2006, 27:3000-3002.

SUMMARY OF THE INVENTION

Problems to be Solved by the Invention

As described above, the problem regarding management of patients with heart failure is an extremely large problem. It is essential to manage patients with heart failure not only at acute medical institutions but also at sites of primary care physicians (local medical care, home medical care). However, natriuretic peptide (BNP) and N-terminal pro-B-type natriuretic peptide (NT-proBNP), which are frequently used as markers reflecting a clinical condition of heart failure at present, require a blood specimen or a certain measurement time, and thus it is not realistic to use them on a daily basis at the stage of a primary care physician. In addition, it is also difficult for a non-cardiologist to manage patients with heart failure while frequently performing echocardiography at the sites of primary care physicians.

Therefore, the present inventors have conducted studies for the purpose of providing a heart failure marker that can be simply and preferably used by non-invasive test.

Means for Solving the Problem

In order to solve the above problems, attention was paid to urine. If a risk of heart failure can be measured by a simple and non-invasive urinalysis, a utility value thereof is very large.

The present inventors have found a possibility that urinary angiotensinogen (ACT) amount is associated with the risk of heart failure, and have further studied.

The present disclosure encompasses, for example, subject matters set forth in the following items:

Item 0.
A method for measuring heart failure risk, comprising:
(A) measuring an angiotensinogen amount value of urine collected from a subject.

Item 1.
A method for measuring heart failure risk, comprising:
(A) measuring an angiotensinogen amount value of urine collected from a subject; and
(B) comparing an angiotensinogen amount value of urine previously collected from a same subject with the angiotensinogen amount value measured in (A).

Item 2.
The method according to item 1, in which the subject is a person in remission of heart failure.

Item 3.
The method according to item 1, in which
the subject is a person in remission of heart failure, and
the urine previously collected is urine collected at a time of remission of heart failure.

Item 4.
The method according to any one of items 1 to 3, in which the angiotensinogen amount value of urine is a value obtained by dividing urinary angiotensinogen mass by urinary creatinine mass.

Item 5.
The method according to any one of items 2 to 4, in which the method is used for prognosis of a person in remission of heart failure, and the subject is a person in remission of heart failure who satisfies at least one of requirements (i) to (iii) below at a time of onset of heart failure.
(i) the subject is 75 years old or older;
(ii) the subject has a history of hypertension;
(iii) the subject has a cardiac function classification (severity) of New York Heart Association (NYHA) of III or higher.

Item 6.
The method according to item 3, in which
when the angiotensinogen amount value of urine is a value obtained by dividing urinary angiotensinogen mass by urinary creatinine mass, and the value is converted into "urinary angiotensinogen mass (µg)/ urinary creatinine mass (g)",
the angiotensinogen amount value of the urine previously collected is 250 or less.

Item 7.
The method according to any one of items 1 to 6, in which the subject is a person who has been admitted due to heart failure, and the urine collected from the subject in (A) is urine collected at a time of revisit or readmission of the subject.

Item 8.
A method for selecting a subject, the method comprising:
(A) measuring an angiotensinogen amount value of urine collected from a subject; and (B) comparing an angiotensinogen amount value of urine previously collected from a same subject with the angiotensinogen amount value measured in (A), in which the subject is a person who has been admitted and discharged due to heart failure, and in a case where the angiotensinogen amount value of urine is a value obtained by dividing urinary angiotensinogen mass by urinary creatinine mass, and the value is converted into "urinary angiotensinogen mass (μg)/urinary creatinine mass (g)", when the angiotensinogen amount value of urine is 1.2 times or more as compared to the angiotensinogen amount value of urine at previous discharge, the subject is selected as a subject with increased heart failure risk as compared to heart failure risk at a time of discharge.

Item 9.

The method according to item 8, in which the subject is a subject whose angiotensinogen amount value of urine at previous discharge is 250 or less.

Item 10.

A kit for measuring heart failure risk, comprising a reagent for measuring angiotensinogen amount and a reagent for measuring creatinine amount.

Item 11.

The kit according to item 10, in which the reagent for measuring angiotensinogen amount comprises an anti-angiotensinogen antibody, and the reagent for measuring creatinine amount comprises picric acid.

Item 12.

The kit according to item 10 or 11, for diagnosis of heart failure, prognosis prediction or prognosis of heart failure, or determination of severity of heart failure.

Item 13.

The kit according to item 10 or 11 for the method according to any of items 1 to 9.

Item A.

A heart failure marker consisting of urinary angiotensinogen.

Item B.

Use of urinary angiotensinogen as a heart failure marker.

Effect of the Invention

According to the present disclosure, a risk of heart failure can be measured by a simple and non-invasive urinalysis. Therefore, for example, it is very useful in management of patients with heart failure, leading to prevention of readmission of patients with heart failure and reduction of medical costs. In addition, for example, regarding cooperation between primary care physicians and acute phase medical institutions, a heart failure marker that can be easily measured on a daily basis is very useful on either side.

Figure 1A:
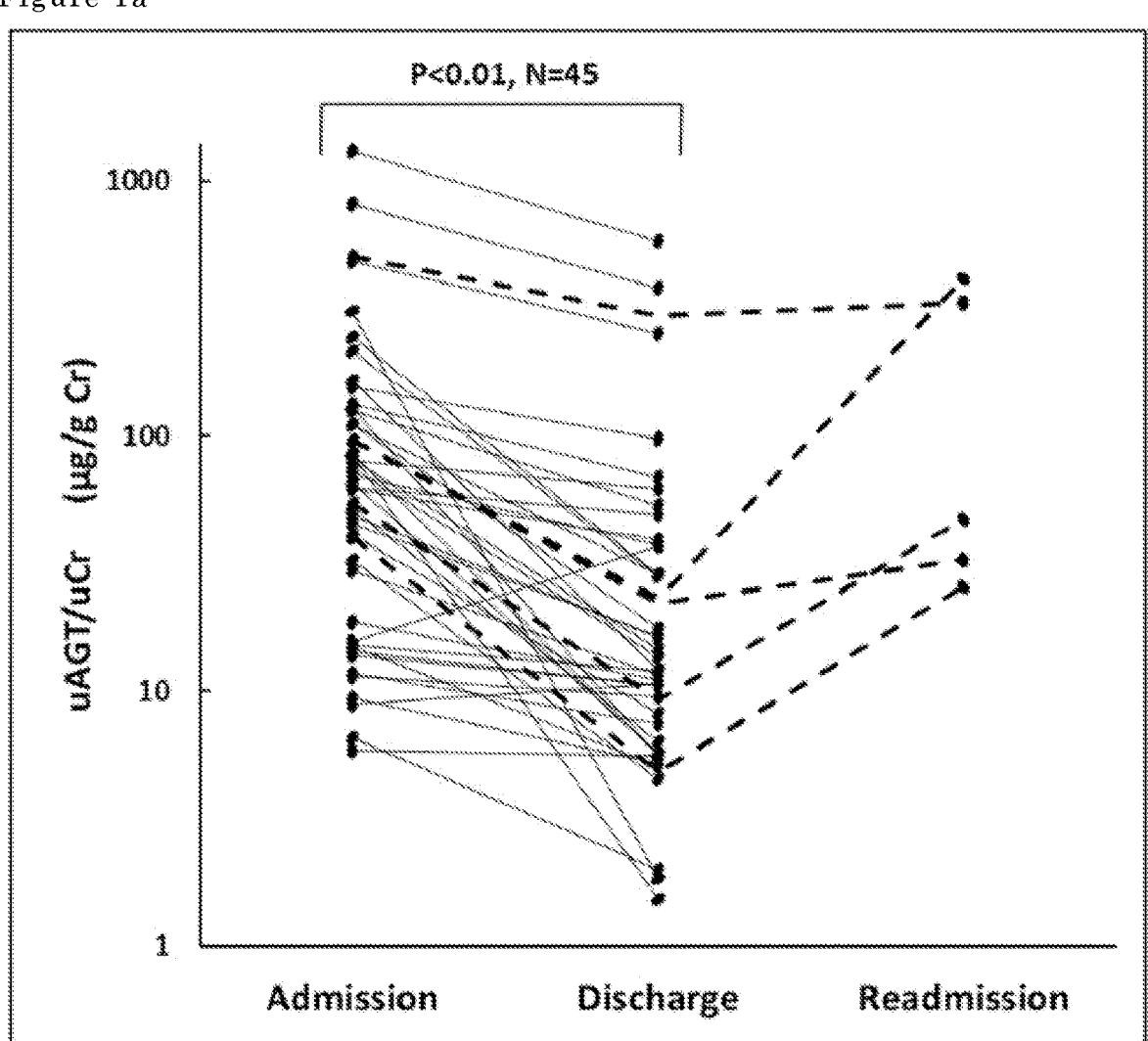
FIG. 1a shows a measurement result of a urinary AGT amount value (urinary AGT mass/urinary Cre mass) of patients hospitalized due to acute heart failure or exacerbation of chronic heart failure.

Cre value and blood NT-proBNP value at discharge, and (C) a correlation between a change in urinary AGT/Cre value (AuATG) from the time of admission at discharge and a change in blood NT-proBNP value (ANT-proBNP) from the time of admission at discharge.

MODE FOR CARRYING OUT THE INVENTION

Hereinafter, each embodiment encompassed by the present disclosure will be described in more detail. The present disclosure preferably encompasses, but is not limited to, a heart failure marker, a method for measuring heart failure risk, and the like, and the present disclosure encompasses all that are disclosed in the present specification and can be recognized by those skilled in the art.

A method for measuring heart failure risk encompassed by the present disclosure includes (A) a step of measuring an angiotensinogen amount value of urine collected from a subject. In the present specification, the method for measuring heart failure risk may be referred to as "the method for measuring heart failure risk of the present disclosure". In addition, the method for measuring heart failure risk of the present disclosure preferably further includes (B) a step of comparing an angiotensinogen amount value of urine previously collected from the same subject with the angiotensinogen amount value measured in the step (A). In the present specification, these steps may be referred to as step (A) and step (B).

The subject is not particularly limited, and may be, for example, a healthy person or a person having risk of heart failure. The person having risk of heart failure is not particularly limited, and examples thereof include a person who is obese or likely to be obese, a person who has hypertension or is likely to have hypertension, an elderly person, a patient with chronic obstructive pulmonary disease (COPD), a smoker, a diabetic patient or a preliminary diabetic, a person in remission of heart failure, and the like.

In particular, the method for measuring heart failure risk of the present disclosure is particularly suitable in a case where the subject is a person in remission of heart failure since a person in remission of heart failure has risk of recurrence of heart failure and it is often necessary to carefully observe the course of the heart failure. From this, it can be said that the method for measuring heart failure risk of the present disclosure can be preferably used particularly for prognosis of a person in remission of heart failure.

When the method for measuring heart failure risk of the present disclosure is used for prognosis of a person in remission of heart failure, it is more preferable that the person in remission of heart failure is a person who satisfies at least one (1, 2, or 3) of the following requirements (i) to (iii) at the time of onset of heart failure. (i) the subject is 75 years old or older, (ii) the subject has a history of hypertension, and (iii) the subject has a cardiac function classification (severity) of New York Heart Association (NYHA) of III or higher.

The angiotensinogen amount value of urine may be a value reflecting an angiotensin amount contained in urine, but is desirably a value preferable for comparison with the angiotensinogen amount value of urine previously collected from the same subject. Preferable examples of such a desirable angiotensinogen amount value include mass or concentration of angiotensinogen in urine collected in one day, a value obtained by dividing urinary angiotensinogen mass by urinary creatinine mass (which may be referred to as "urinary AGT/Cre value" in the present specification) in a certain amount of urine, and the like. From the viewpoint of convenience, the urinary AGT/Cre value is particularly preferable. The urinary AGT/Cre value may be determined, for example, using urine obtained in one urine collection or using pooled urine obtained by a plurality of urine collections. From the viewpoint of convenience, it is preferable to determine the urinary AGT/Cre value using urine obtained in one urine collection. A method for calculating the urinary AGT/Cre value is not particularly limited. For example, it may be determined by dividing urinary angiotensinogen mass by urinary creatinine mass, or may be determined by dividing urinary angiotensinogen concentration by urinary creatinine concentration.

A method for measuring angiotensinogen mass and creatinine mass in urine and the like is not particularly limited, and can be measured by a known method. Examples thereof include an ELISA method, an immunochromatography method, and the like. In addition, for example, Jaffe method can be used to measure creatinine amount. For these measurements, a commercially available measurement kit may be used. For example, Human Total Angiotensinogen Assay Kit (Immuno-Biological Laboratories Co, Ltd.) or the like can be used for measurement of angiotensinogen mass. In addition, for example, for measurement of creatinine mass, LabAssay creatinine (FUJIFILM Wako Pure Chemical Corporation) or the like can be used.

Since the angiotensinogen amount value of urine varies among individuals, it is preferable to perform risk measurement according to a change in value in each individual. When the angiotensinogen amount value of urine is higher than the angiotensinogen amount value of urine previously collected, it can be determined that heart failure risk has been increased as compared to a time when the urine was previously collected. Conversely, when the angiotensinogen amount value of urine is lower than the angiotensinogen amount value of urine previously collected, it can be determined that heart failure risk has been reduced as compared to a time when the urine was previously collected.

In particular, it is preferable to determine that the risk has changed when the angiotensinogen amount value is changed by 1.2 times or more as compared to the angiotensinogen amount value of urine previously collected. It is more preferable to determine that the risk has changed when the change in the value is 1.3 times or more, 1.4 times or more, 1.5 times or more, 1.6 times or more, 1.7 times or more, 1.8 times or more, 1.9 times or more, or 2 times or more. It is further preferable to determine that the risk has changed when the change in the value is 2.5 times or more, 3 times or more, 3.5 times or more, 4 times or more, 4.5 times or more, or 5 times or more.

In particular, when the urinary AGT/Cre value is used as the angiotensinogen amount value, it is preferable to determine that the risk has changed when the urinary AGT/Cre value has changed by 1.2 times or more as compared to the AGT/Cre value of urine previously collected. It is more preferable to determine that the risk has changed when the change in the value has changed 1.3 times or more, 1.4 times or more, 1.5 times or more, 1.6 times or more, 1.7 times or more, 1.8 times or more, 1.9 times or more, or 2 times or more. It is further preferable to determine that the risk has changed when the change in the value is 2.5 times or more, 3 times or more, 3.5 times or more, 4 times or more, 4.5 times or more, or 5 times or more.

In addition, in the method for measuring heart failure risk of the present disclosure, preferably, an angiotensinogen amount value of urine previously collected from the same subject is compared to the angiotensinogen amount value measured in the step (A) (step (B)), and the previously collected urine may be urine collected once or a plurality of times. For example, when urine is collected once before to measure an angiotensinogen amount value, heart failure risk can be measured by further collecting urine to measure an angiotensinogen amount value and comparing the amount value with a previous value, and when urine is collected a plurality of times before to measure an angiotensinogen amount value, transition of heart failure risk can also be monitored by further collecting urine to measure an angiotensinogen amount value and comparing the amount value with each previous value.

The present disclosure can be particularly preferably used for performing heart failure risk management, for example, after a heart failure inpatient is ameliorated and discharged. As described above, it is essential to manage patients with heart failure also at sites of primary care physicians (local medical care, home medical care) after discharge, and the method for measuring heart failure risk of the present disclosure is effective because there has been no heart failure marker that can be used daily at such sites so far. Among them, it is possible to easily measure heart failure risk periodically after discharge, for example, by collecting urine at the time of remission of heart failure (more specifically, for example, at the time of discharge), (then, preferably by measuring the angiotensinogen amount value in the urine). In addition, the method of the present disclosure is also useful for determining recurrence and/or deterioration of heart failure for a patient who is to revisit or to be readmitted after discharge. If the patient is determined to be recurrent and/or deteriorated at the time of revisit, appropriate treatment such as readmission can be promptly performed. Even after readmission, it can be preferably used for monitoring heart failure risk.

In a case where the method for measuring heart failure risk of the present disclosure is used for a person in remission of heart failure (preferably, a person in remission of heart failure who has experienced remission and discharge after being hospitalized due to heart failure), using a urinary AGT/Cre value as an angiotensinogen amount value, when the urinary AGT/Cre value is converted to "urinary AGT mass (μg)/urinary Cre mass (g)", the urinary AGT/Cre value at onset of heart failure (particularly at admission) is preferably 500 or less, and more preferably 450 or less, 400 or less, 350 or less, 300 or less, 250 or less, 200 or less, 150 or less, or 100 or less. The lower limit of the value is not particularly limited, and is, for example, 20, 25, 30, or 35 or more. In addition, when urinary AGT/Cre values are calculated in the same manner, the urinary AGT/Cre value at the time of remission (particularly at the time of discharge) is preferably 250 or less, more preferably 200 or less, 150 or less, or 100 or less, and further preferably 90, 80, 70, 60, 50, or 40 or less. The lower limit of the value is not particularly limited, and is, for example, 1, 2, 3, or 4 or more. In addition, when urinary AGT/Cre values are similarly calculated, it is preferable to determine that the risk has been increased when the urinary AGT/Cre value changes by 1.2 times or more as compared to the urinary AGT/Cre value collected at the time of discharge, and it is more preferable to determine that the risk has been increased when the urinary AGT/Cre value changes by 1.3 times or more, 1.4 times or more, 1.5 times or more, 1.6 times or more, or 1.7 times or more as compared to the urinary AGT/Cre value. The same determination can be made in a case where the urinary AGT/Cre value changes by 2 times or more, 2.5 times or more, or 3 times or more as one form. Furthermore, in this case, the subject person in remission of heart failure is more preferably a person who satisfies at least one of the above requirements (i) to (iii).

In addition, when the method for measuring heart failure risk of the present disclosure is used for a person in remission of heart failure (preferably, a person in remission of heart failure who has experienced remission and discharge after being hospitalized due to heart failure), using the urinary AGT concentration value as the angiotensinogen amount value, the AGT concentration in urine is preferably 300, 250, 200, or 150 ng/ml or less, and more preferably 140, 130, 120, 110, or 100 ng/ml or less at onset of heart failure (particularly at admission). The lower limit of the concentration is not particularly limited, and is, for example, 1, 2, 3, or 4 ng/ml or more. In addition, it is preferable to determine that the risk has been increased when the AGT concentration in urine changes by 1.5 or more from the AGT concentration in urine collected at the time of discharge, and it is more preferable to determine that the risk has been increased when the AGT concentration in urine changes by 1.6, 1.7, 1.8, 1.9, or 2 or more. Furthermore, in this case, the subject person in remission of heart failure is more preferably a person who satisfies at least one of the above requirements (i) to (iii).

Moreover, it is more preferable to use both the urinary AGT/Cre value and the urinary AGT concentration value in combination for measuring the risk.

Further, regarding the urinary AGT/Cre value, when a change rate is calculated by the following formula:

Change Rate (%)=(Value at Readmission−Value at Discharge)/Value at Discharge×100 the change rate is preferably 40, 45, or 50% or more, and more preferably 100, 150, or 200% or more.

Furthermore, when a change rate is similarly calculated for the AGT concentration (ng/ml) in urine, the change rate is preferably 50, 55, 60, or 65% or more, and more preferably 70, 80, 90, or 100% or more.

In the present specification, the heart failure risk may be rephrased as the risk of heart failure, and measuring risk of heart failure refers to measuring risk of developing heart failure when the subject is a person who does not develop heart failure or a person in remission of heart failure, or the like, and refers to measuring severity when the subject is a person who develops heart failure, or the like.

For example, by measuring heart failure risk by the method for measuring heart failure risk of the present disclosure, diagnosis of heart failure (particularly diagnosis of recurrence of heart failure) or monitoring of the course of prognosis of heart failure can be easily performed. Therefore, it is also useful for prognosis prediction or prognosis. Alternatively, it can also be used as an index for determining the severity when suffered (particularly recurred) from heart failure. In addition, for example, it is also useful for selecting urine derived from a subject having an increased heart failure risk, and thus selecting the subject having an increased heart failure risk. If a subject having an increased heart failure risk can be early selected by the method for measuring heart failure risk of the present disclosure, it is possible to perform careful follow-up and early treatment of heart failure (for example, administration of a drug for treating heart failure).

Heart failure causes a person to suffer from symptoms such as swelling and shortness of breath. Anxiety and hardship associated with gradual progression of symptoms of heart failure also occur. Furthermore, lifetime of the patient itself may be shortened (poor prognosis). With respect to the degree of each item, it is expected that information can be obtained by measuring the risk of developing heart failure and/or the severity of heart failure using the method for measuring heart failure risk of the present disclosure.

The present disclosure also encompasses a heart failure marker consisting of urinary angiotensinogen and use of urinary angiotensinogen as a heart failure marker. As described above, the heart failure risk can be easily measured by using the urinary angiotensinogen amount value, and the heart failure marker is useful for the measurement. By using the heart failure marker, as described above, diagnosis of heart failure (in particular, diagnosis of recurrence of heart failure) or monitoring of the course of prognosis of heart failure can be easily performed. Therefore, it is also useful for prognosis prediction or prognosis. Alternatively, it is useful for determining the severity of heart failure when suffered (particularly recurred) from heart failure.

Furthermore, the present disclosure also encompasses a kit for measuring heart failure risk, including a reagent for measuring angiotensinogen amount. The kit preferably further includes a reagent for measuring creatinine amount. Also, the reagent for measuring angiotensinogen amount is preferably a reagent for measuring urinary angiotensinogen amount. The reagent for measuring creatinine amount is preferably a reagent for measuring urinary creatinine amount. In addition, it is preferable that the reagent for measuring angiotensinogen amount contains an anti-angiotensinogen antibody. Angiotensinogen amount in urine can be preferably measured by an anti-angiotensinogen antibody, by an ELISA method, an immunochromatography method, or the like. Moreover, the reagent for measuring creatinine amount preferably contains picric acid. By using picric acid, creatinine amount in urine can be preferably measured based on the Jaffe method.

In the present specification, the term "comprising" also includes "consisting essentially of" and "consisting of." In addition, the present disclosure encompasses any combination of the components described in the present specification.

Furthermore, various characteristics (properties, structures, functions, and the like) described for each embodiment of the present disclosure described above may be combined in any manner in specifying the subject matter encompassed by the present disclosure. That is, the present disclosure encompasses all subject matter consisting of any combination of combinable properties described herein.

EXAMPLES

Hereinafter, the present disclosure will be described more specifically, but the present disclosure is not limited to the following examples.

Among patients who were 18 years old or older and who were hospitalized in the Emergency Medical Center or the cardiovascular center of Kagawa University Hospital due to acute heart failure or exacerbation of chronic heart failure, patients who survived and left the hospital (45 patients; average age of about 76 years) were examined.

Urine specimen and blood specimen of a subject patient were collected and examined for measurement of urinary angiotensinogen (AGT) and NT-proBNP at admission and before discharge when hemodynamics were stabilized and clinical improvement was obtained. The obtained specimens of casual urine were stored at −80° C. after centrifugation. Thereafter, the urinary AGT value was measured by an ELISA method using an ELISA kit (#27412 Human Total Angiotensinogen Assay Kit: Immuno-Biological Laboratories Co, Ltd.). In addition, the blood NT-proBNP amount was measured using a kit for measuring human NT-proBNP "Elecays (registered trademark) reagent NT-proBNP II" (Roche Diagnostics).

In addition, a urinary creatinine (Cre) value (mg/dL) was measured using an assay kit (290-65901, LabAssay creatinine: FUJIFILM Wako Pure Chemical Corporation), and creatinine correction was performed by dividing the urinary AGT (u-AGT) value (ng/mL) by the urinary Cre value and multiplying it by 100 (urinary AGT/Cre value). That is, for creatinine correction in casual urine, creatinine excretion amount in one day was assumed to be 1 g, and ACT content (μg) per urine with respect to 1 g of creatinine excreted was calculated. Therefore, when showing the results, the unit was referred to as "μg/g Cr".

Figure 1B:
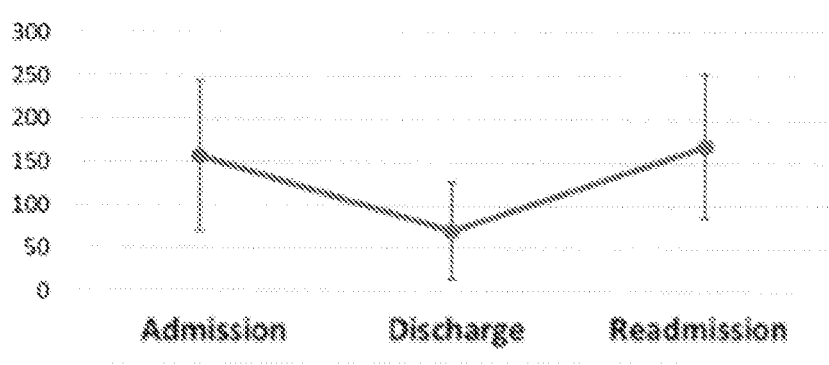
FIG. 1b shows graphs summarizing each of a change in urinary AGT/Cre value and a change in NT-proBNP for readmission patients.
Figure 1B:
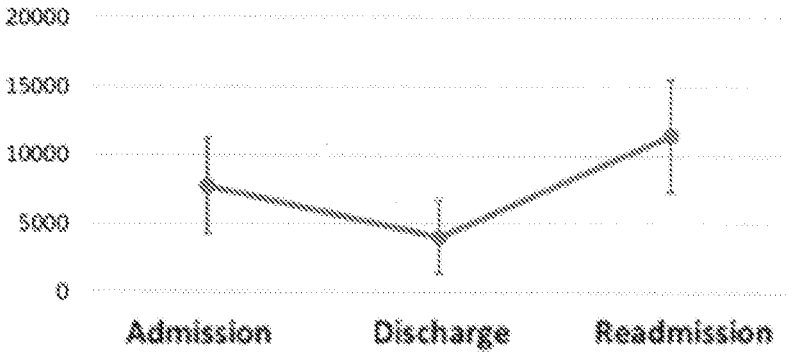

The results are shown in FIG. 1a. In FIG. 1a, the urinary ACT/Cre value is referred to as "uAGT/uCr". Also, FIG. 1a shows urinary AGT/Cre values at admission and discharge. Since five subject patients were readmitted, urinary AGT/Cre values at readmission are also shown. In addition, for the data of the five subjects, graphs each summarizing variation in urinary AGT/Cre value and variation in NT-proBNP are shown in FIG. 1b. Analysis using a mixed effect model confirmed that a series of movements in the graph of FIG. 1b was statistically significantly correlated.

Similarly to NT-proBNP, it could be confirmed that the value of urinary AGT decreased at discharge as compared to the value at admission, in conjunction with the therapeutic effect (improvement in heart failure control). In addition, in particular, the readmission example is indicated by a broken line, and it could be confirmed that the value increased again as in the case of the first admission. Moreover, it was found that these decreases and re-increases were accompanied by a change of about 1.2 to 5 times.

For subject patient 5 who was readmitted, the urinary AGT/Cre values (specifically, "urinary AGT mass (μg)/urinary Cre mass (g)") and the urinary AGT concentration values (ng/mL) at admission, discharge, and readmission are shown in the following tables. The tables also show values of change rate r) and change amount calculated by the following equations.

Change Rate (%)=(Value at Readmission−Value at Discharge)/Value at Discharge×100

Change Amount=Value at Readmission/Value at Discharge

The subject patients who were readmitted were all 75 years old or older, had a history of hypertension, and had a cardiac function classification (severity) according to NYHA (New York Heart Association) of III or higher.

TABLE 1A

| Subject patient | uAGT/uCre (ug/g Cre) | | | Change rate | Change amount |
| | At admission (1) | At discharge (2) | At readmission (3) | (2)→(3) | (2)→(3) |
|---|---|---|---|---|---|
| 1 | 39.8 | 4.8 | 25.6 | 432.2 | 5.3 |
| 2 | 502.2 | 296.7 | 331.7 | 11.8 | 1.1 |
| 3 | 95.4 | 22.0 | 32.6 | 48.4 | 1.5 |
| 4 | 54.7 | 9.2 | 47.5 | 414.8 | 5.1 |
| 5 | 96.2 | 23.1 | 415.2 | 1695.5 | 18 |

TABLE 1B

| Subject patient | uAGT (ng/mL) | | | Change rate | Change amount |
| | At admission (1) | At discharge (2) | At readmission (3) | (2)→(3) | (2)→(3) |
|---|---|---|---|---|---|
| 1 | 40.4 | 2.9 | 17.3 | 489.9 | 5.9 |
| 2 | 265.5 | 188.2 | 180.7 | −4.0 | 1.0 |
| 3 | 27.5 | 9.5 | 15.9 | 66.7 | 1.7 |
| 4 | 5.5 | 2.0 | 19.9 | 883.4 | 9.8 |
| 5 | 93.6 | 12.2 | 351.6 | 2780.8 | 28.8 |

Figure 2:
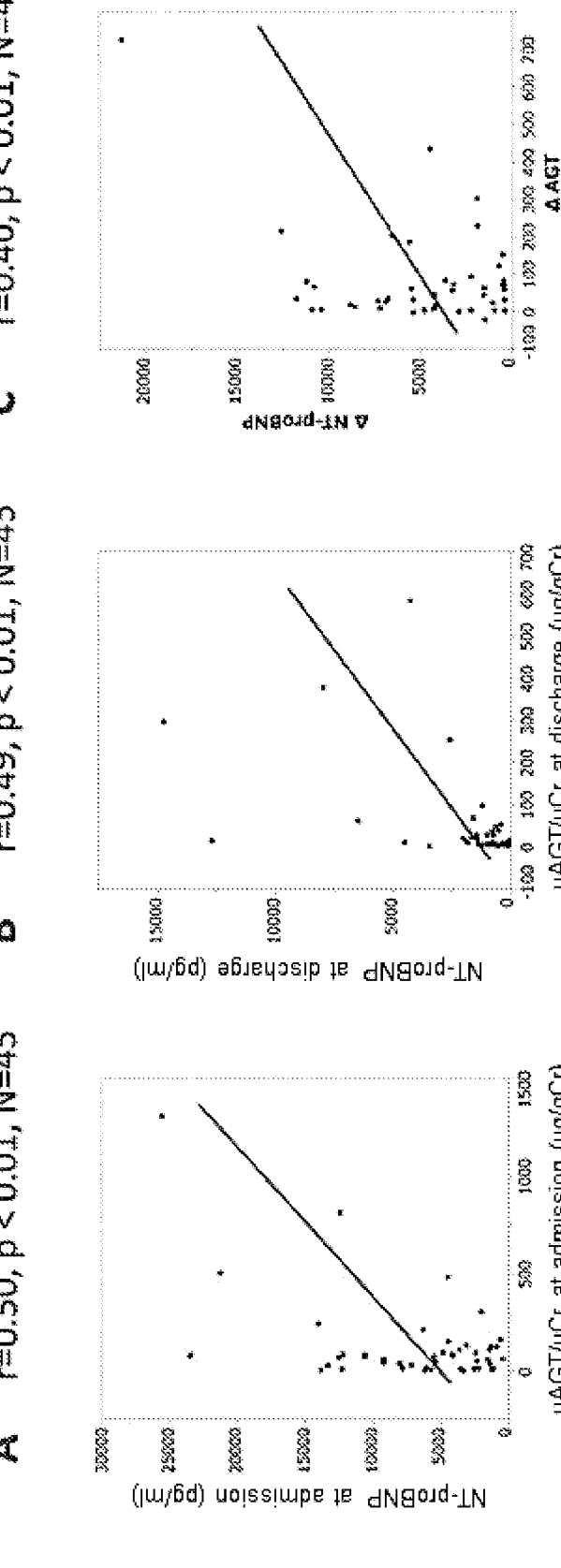
FIG. 2 shows results of studies on (A) a correlation between urinary AGT/Cre value and blood NT-proBNP value at admission, (B) a correlation between urinary AGT/

Furthermore, (A) a correlation between urinary AGT/Cre value and blood NT-proBNP value at admission, (B) a correlation between urinary AGT/Cre value and blood NT-proBNP value at discharge, and (C) a correlation between a change in urinary AGT/Cre value (AuATG) from the time of admission at discharge and a change in blood NT-proBNP value (ANT-proBNP) from the time of admission at discharge were examined. The results are shown in FIG. 2. As shown in FIG. 2, a correlation was observed in any of the above (A), (B), and (C) (there was a significant difference).

The blood NT-proBNP amount is widely accepted as an important reference with high accuracy of diagnosis and evaluation in diagnosis, severity, prognosis prediction, prognosis and the like of heart failure (that is, it is the golden standard). Since a correlation was observed between the blood NT-proBNP value and the urinary AGT/Cre value, it is considered that the urinary AGT/Cre value can be used as a particularly excellent (accuracy in diagnosis, severity, prognosis prediction, prognosis and the like of heart failure are high) reference.

Furthermore, the urinary AGT/Cre values (specifically, "urinary ACT mass (μg)/urinary Cre mass (g)") and the urinary AGT concentration values (ng/mL) at admission, discharge and readmission, in 4 patients who were admitted in the same center due to heart failure and discharged but were readmitted, measured in the same manner as described above in another period, are shown in the following tables. The tables also show values of change rate (%) and change amount calculated in the same manner as described above.

TABLE 2A

| Subject patient | uAGT/uCre (ug/g Cre) | | | Change rate | Change amount |
| | At admission (1) | At discharge (2) | At readmission (3) | (2)→(3) | (2)→(3) |
|---|---|---|---|---|---|
| 1a | 10.6 | 5.1 | 28.6 | 463.7 | 5.6 |
| 2a | 96.0 | 33.7 | 114.4 | 239.3 | 3.4 |
| 3a | 19.6 | 7.9 | 26.7 | 236.9 | 3.4 |
| 4a | 238.9 | 9.5 | 49.9 | 428.2 | 5.3 |

TABLE 2B

| Subject patient | uAGT (ng/mL) | | | Change rate | Change amount |
| | At admission (1) | At discharge (2) | At readmission (3) | (2)→(3) | (2)→(3) |
|---|---|---|---|---|---|
| 1a | 6.6 | 3.5 | 7.1 | 103.1 | 2.0 |
| 2a | 51.5 | 29.5 | 82.4 | 178.9 | 2.8 |
| 3a | 21.8 | 9.5 | 15.8 | 66.9 | 1.7 |
| 4a | 58.6 | 3.1 | 17.3 | 463.1 | 5.6 |

From these, it was found that the risk of heart failure can be measured by using the urinary AGT amount value, particularly the urinary AGT concentration value or the urinary AGT/Cre value.

In particular, it was considered that the change amount of the urinary AGT concentration value of 1 or more, more preferably 1.5 or more suggests that possibility of readmission is high. In addition, it was considered that the change amount of the urinary AGT/Cre value of 1 or more, more preferably 1.5 or more suggests that possibility of readmission is high.

In subject patient 2 in Tables 1A and 1B above, it was presumed that renal function remarkably deteriorated as compared to the other four patients (1, 3, 4, and 5), and thus the values of the change rate and the change amount were smaller than those of the other patients.

The invention claimed is:

1. A method of treating or preventing heart failure in a subject identified as having an increased urinary angiotensinogen amount value, the method comprising:
   administering a heart failure drug to the subject identified as having an increased urinary angiotensinogen amount value for treating or preventing heart failure,
   wherein the urinary angiotensinogen amount value is a value obtained by measuring an angiotensinogen amount and a creatinine amount in a urine sample collected from the subject at a defined time and dividing urinary angiotensinogen mass by urinary creatinine mass, and the value is converted into "urinary angiotensinogen mass (μg)/urinary creatinine mass (g)", and
   wherein the subject is identified as having an increased urinary angiotensinogen amount value when the measured urinary angiotensinogen amount value is 1.2 times or more than the value measured in a urine sample collected from the subject prior to the defined time.

2. The method according to claim 1, wherein
   the subject is further a person having risk of heart failure, and the subject is further a person in remission of heart failure, a person who is obese or likely to be obese, a person who has hypertension or is likely to have hypertension, an elderly person, a patient with chronic obstructive pulmonary disease (COPD), a smoker, a diabetic patient or a preliminary diabetic, or
   the subject is further a patient with heart failure, and the subject is further a patient with acute heart failure or a patient with exacerbation of chronic heart failure.

3. The method according to claim 1, wherein
   the subject is further a person having risk of heart failure, and the subject is further a person in remission of heart failure, and
   the urine sample collected from the subject prior to the defined time is urine collected at a time of remission of heart failure.

4. The method according to claim 1, wherein the subject is further a person having risk of heart failure, and the subject is further a person in remission of heart failure and the person satisfies at least one of requirements i), (ii) and (iii) below at a time of onset of the heart failure:
   (i) the subject is 75 years old or older;
   (ii) the subject has a history of hypertension;
   (iii) the subject has a cardiac function classification severity of New York Heart Association (NYHA) of III or higher.

5. The method according to claim 1, wherein
   the angiotensinogen amount value of the urine sample collected from the subject prior to the defined time is 250 or less.

6. The method according to claim 1, wherein
   the subject is further a person who has been hospitalized for acute heart failure, or hospitalized for exacerbation of chronic heart failure,
   the subject has been further hospitalized, and
   the urine sample collected from the subject at the defined time is urine collected when the subject is further hospitalized.

7. The method according to claim 1, wherein
   the urinary angiotensinogen amount value is measured by using a kit comprising a reagent for measuring an angiotensinogen amount and a reagent for measuring a creatinine amount.

8. The method according to claim 7,
   wherein the reagent for measuring the angiotensinogen amount comprises an anti-angiotensinogen antibody, and
   the reagent for measuring the creatinine amount comprises picric acid.

9. The method according to claim 1, wherein the angiotensinogen amount value measured in in the urine sample collected from the subject at the defined time is 3.0 times or more the angiotensinogen amount value of the urine sample collected from the subject prior to the defined time.

* * * * *